(12) United States Patent
Ranger et al.

(10) Patent No.: US 6,939,564 B2
(45) Date of Patent: *Sep. 6, 2005

(54) WATER-SOLUBLE STABILIZED SELF-ASSEMBLED POLYELECTROLYTES

(75) Inventors: Maxime Ranger, Rigaud (CA); Jean-Christophe Leroux, Montreal (CA)

(73) Assignee: Labopharm, Inc., Quebec (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/877,999

(22) Filed: Jun. 8, 2001

(65) Prior Publication Data

US 2003/0059398 A1 Mar. 27, 2003

(51) Int. Cl.[7] .......................... C08E 297/00; A61K 9/50
(52) U.S. Cl. ........................... 424/497; 525/280
(58) Field of Search ............................. 525/280–323; 424/497, 70.1–70.9, 78.08

(56) References Cited

U.S. PATENT DOCUMENTS

| | | | |
|---|---|---|---|
| 5,510,103 A | * | 4/1996 | Yokoyama ............... 424/78.08 |
| 5,620,850 A | | 4/1997 | Bamdad et al. |
| 5,656,611 A | | 8/1997 | Kabanov et al. |
| 5,693,751 A | | 12/1997 | Sakurai et al. |
| 5,702,717 A | | 12/1997 | Cha et al. |
| 5,770,627 A | | 6/1998 | Inoue et al. |
| 5,786,387 A | | 7/1998 | Watanabe et al. |
| 5,840,319 A | | 11/1998 | Alakhov et al. |
| 5,908,777 A | | 6/1999 | Lee et al. |
| 5,925,720 A | | 7/1999 | Kataoka et al. |
| 5,929,177 A | | 7/1999 | Kataoka et al. |
| 5,939,453 A | | 8/1999 | Heller et al. |
| 5,955,509 A | | 9/1999 | Webber et al. |
| 6,217,912 B1 | | 4/2001 | Park et al. |
| 6,221,959 B1 | | 4/2001 | Kabanov et al. |
| 6,372,203 B1 | * | 4/2002 | Allwohn ............... 424/70.13 |
| 6,440,743 B1 | * | 8/2002 | Kabanov ............... 435/458 |
| 2002/0187199 A1 | * | 12/2002 | Ranger et al. ............ 424/501 |

FOREIGN PATENT DOCUMENTS

| | | |
|---|---|---|
| EP | 0 963 758 A2 | 12/1999 |
| WO | WO 96/21036 | 7/1996 |
| WO | WO 96/32841 | 10/1996 |
| WO | WO 97/33737 | 9/1997 |
| WO | WO 98/19710 | 5/1998 |
| WO | WO 98/37902 | 9/1998 |

OTHER PUBLICATIONS

GenBank Accession No. AAA21101, published Aug. 6, 1994) retrieved from http://www.ncbi.nlm.nih.gov:80/entrez/viewer.fcgi?db=protein&val=532507 on Mar. 30, 2004.*

GenBank Accession No. CAA23748, published Mar. 24, 1993), retrieved from http://www.ncbi.nlm.nih.gov:80/entrez/viewer.fcgi?db=protein&val=51618 on Mar. 30, 2004.*

Benahmed (Pharmaceutical Research, vol. 18, No. 3, 2001, pp. 323–328).*

Jones et al. (European J. of Pharm. Biopharm. 48, 101–11 1, 1999).*

Heller et al (J. Pharm. Sci. 88(1): 58–64, 1999).*

(Continued)

*Primary Examiner*—Dave Trong Nguyen
*Assistant Examiner*—Richard Schnizer
(74) *Attorney, Agent, or Firm*—McHale & Slavin, P.A.

(57) ABSTRACT

The present invention is directed toward water-soluble supramolecular self-assemblies and a process for their preparation via micellization of polyelectrolytes through the use of hydrophobic monomeric units. In this invention the polyelectrolyte segment ultimately forms the core of the supramolecular assembly whereas the shell consists of uncharged hydrophilic polymers or oligomers. It has been determined that the inclusion of the hydrophobic co-monomers to the polyelectrolyte segment forming the micelle core leads to a structure of enhanced stability.

11 Claims, 4 Drawing Sheets

The synthetic route for the preparation of block copolymer, possessing a hydrophobized polyelectrolyte block.

OTHER PUBLICATIONS

Stryer (In Biochemistry, Fourth edition, W.H. Freeman and Co., New York, 1995).*

Jones et al., Polymeric micelles—a new generation of colloidal drug carriers, Eur. J. Pharmaceut. Biopharmaceut., (1999) 48, pp101–111.

Kwon et al., Polymeric micelles as new drug carriers, Adv. Drug Deliv. Rev., (1996) 21, pp107–116.

Allen et al., Nano—engineering block copolymer aggregates for drug delivery, Colloids Surf. B, (1999) 16, pp3–27.

Zhao et al., Fluorescence probe techniques used to study micelle formation in water–soluble block copolymers, Langmuir, (1990) 6, pp514–516.

Kabanov et al., The neuroleptic activity of haloperidol increases after its solubilization in surfactant micelles: Micelles as microcontainers for drug targeting, FEBS, (1989) 258, 2, pp343–345.

Zhang et al., Multiple morphologies of"crew—cut" aggregates of polystyrene –b– poly (acrylic acid), Science, (1995), 268, pp1728–1731.

Inoue et al., An AB block copolymer of oligo(methyl methacrylate) and poly(acrylic acid) for micellar delivery of hydrophobic drugs, J. Controlled Release, (1998) 51, pp221–229.

Kataoka, Design of nanoscopic vehicles for drug targeting based on micellization of amphiphilic block copolymers, J. Macromol. Sci.—Pure Appl. Chem., (1994) A31, 11, pp1759–1769.

Kataoka et al., Doxorubicin–loaded poly(ethylene glycol)–poly(β–benzyl–L–aspartate) copolymer micelles: their pharmaceutical characteristics and biological significance, J. Controlled Release, (2000) 64, pp143–153.

Benahmed et al., Novel polymeric micelles based on the amphiphilic diblock copolymer poly(N–vinyl–2–pyrrolidone)–block–poly(D,L–lactide), Pharmaceut. Res., (2001) 18, 3, pp323–328.

Lee et al., Synthesis and micellar characterization of amphiphilic diblock copolymers based on poly(2–ethyl–2–oxazoline) and aliphatic polyesters, Macromol., (1999) 32, pp1847–1852.

Scholz et al., A novel reactive polymeric micelle with aldehyde groups on its surface, Macromol., (1995) 28, pp7295–7297.

Lele et al., Mucoadhesive drug carriers based on complexes of poly(acrylic acid) and PEGylated drugs having hydrolysable PEG–anhydride–drug linkages, J. Controlled Release, (2000) 69, pp237–248.

Kataoka et al., Spontaneous formation of polyion complex micelles with narrow distribution from antisense oligonucleotide and cationic block copolymer in physiological saline, Macromol., (1996) 29, pp8556–8557.

Kakizawa et al., Environment–sensitive stabilization of core–shell structured polyion complex micelle by reversible cross–linking of the core through disulfide bond, J. Am. Chem.Soc., (1999) 121, pp11247–11248.

Coessens et al., Functional polymers by atom transfer radical polymerization, Prog. Polym. Sci., (2001) 26, pp337–377.

* cited by examiner

The synthetic route for the preparation of block copolymer, possessing a hydrophobized polyelectrolyte block.

Figure 2. $^1$H NMR spectrum of PEG-*b*-P(DMAEMA$_{30}$-*co*-EMA$_{70}$) in CDCl$_3$.

The variation in light scattering and pyrene fluorescence $I_{338}/I_{333}$ ratio of a PEG-$b$-P(EA$_{50}$-$co$-MAA$_{50}$) aqueous solution as a function of pH.

$^1$H NMR spectrum of PEG-b-P(EA$_{50}$-co-MAA$_{50}$) in D$_2$O at pH 10 (A) and at pH 3 (B).

WATER-SOLUBLE STABILIZED SELF-ASSEMBLED POLYELECTROLYTES

FIELD OF THE INVENTION

This invention generally relates to the preparation of water-soluble self-assemblies, particularly to the association of ionizable or permanently-charged copolymers, and most particularly to the inclusion of hydrophobic comonomers to the polyelectrolyte segment forming the assembly core.

BACKGROUND OF THE INVENTION

In order to improve the specific delivery of drugs with a low therapeutic index, several drug carriers such as liposomes, microparticles, nano-associates (e.g. polymeric micelles, polyion complex micelles (PICM)) and drug-polymer conjugates have been studied. In recent years, water-soluble supramolecular assemblies such as polymeric micelles and PICM have emerged as promising new colloidal carriers for the delivery of hydrophobic drugs and polyions (e.g. antisense oligonucleotides), respectively.

Polymeric micelles have been the object of growing scientific attention, and have emerged as potential carriers for drugs having poor water solubility because they can solubilize those drugs in their inner core and they offer attractive characteristics such as a generally small size (<300 nm) and a propensity to evade scavenging by the mononuclear phagocyte system.

Micelles are often compared to naturally occurring carriers such as viruses or lipoproteins. All three of these carriers demonstrate a similar core-shell structure that allows for their contents to be protected during transportation to the target cell, whether it is DNA for viruses or water-insoluble drugs for lipoproteins and micelles.

Polymeric micelles seem to be one of the most advantageous carriers for the delivery of poorly water-soluble drugs as reported by Jones and Leroux, *Eur. J. Pharm. Biopharm.* (1999) 48, 101–111; Kwon and Okano, *Adv. Drug Deliv. Rev.* (1996) 21, 107–116 and Allen et al. *Colloids Surf. B: Biointerf.* (1999) 16, 3–27. They are characterized by a core-shell structure. The hydrophobic inner core generally serves as a microenvironment for the solubilization of poorly water-soluble drugs, whereas the hydrophilic outer shell is responsible for micelle stability, protection against opsonization, and uptake by the mononuclear phagocyte system.

Pharmaceutical research on polymeric micelles has been mainly focused on copolymers having an AB diblock structure with A, the hydrophilic shell moieties and B the hydrophobic core polymers, respectively. Multiblock copolymers such as poly(ethylene oxide)-poly(propylene oxide)-poly(ethylene oxide) (PEO-PPO-PEO) (A-B-A) can also self-organize into micelles, and have been described as potential drug carriers, e.g. Kabanov et al., *FEBS Lett.* (1989) 258, 343–345. The hydrophobic core which generally consists of a biodegradable polymer such as a poly(β-benzyl-aspartate) (PBLA), poly(D,L-lactic acid) or poly(ε-caprolactone), serves as a reservoir for a poorly water-soluble drug, protecting it from contact with the aqueous environment. The core may also consist of a water-soluble polymer, such as poly(aspartic acid) (P (Asp)), which is rendered hydrophobic by the chemical conjugation of a hydrophobic drug, or is formed through the association of two oppositely charged polyions (PICM). Several studies also describe the use of poorly or non-biodegradable polymers, such as polystyrene (PSt) or poly (methyl methacrylate) (PMMA), as constituents of the inner core. See, e.g., Zhao et al., *Langmuir* (1990) 6, 514–516; Zhang et al., *Science* (1995) 268, 1728–1731; Inoue et al., *J. Controlled Release* (1998) 51, 221–229 and Kataoka *J. Macromol. Sci. Pure Appl. Chem.* (1994) A31, 1759–1769. The hydrophobic inner core can also consist of a highly hydrophobic small chain such as an alkyl chain or a diacyl-lipid (e.g. distearoyl phosphatidyl ethanolamine). The hydrophobic chain can be either attached to one end of a polymer, or randomly distributed within the polymeric structure. The shell usually consists of chains of hydrophilic, non-biodegradable, biocompatible polymers such as poly(ethylene oxide) (PEO) (see Allen et al. *Colloids Surf. B: Biointerf.* (1999) 16, 3–27 and Kataoka et al. *J. Controlled Release* (2000) 64, 143–153), poly(N-vinyl-2-pyrrolidone) (PVP) (see Benahmed A et al. *Pharm Res* (2001) 18, 323–328) or poly(2-ethyl-2-oxazoline) (see Lee et al. *Macromolecules* (1999) 32, 1847–1852).

The biodistribution of the carrier is mainly dictated by the nature of the hydrophilic shell. Other polymers such as poly(N-isopropylacrylamide) and poly(alkylacrylic acid) impart temperature or pH sensitivity to the micelles, and could eventually be used to confer bioadhesive properties (see U.S. Pat. No. 5,770,627). Micelles presenting functional groups at their surface for conjugation with a targeting moiety have also been described (See, e.g., Scholz, C. et al., *Macromolecules* (1995) 28, 7295–7297).

At the present time, most polymeric micelles described in the literature are prepared using non-ionizable block polymers or block copolymers where ionizable monomers are used to form the micelle corona whereas the core consists of a hydrophobic neutral homopolymer or copolymer. Ionizable diblock copolymers have been shown to exhibit pH-dependent micellization. Recently, Webber and Martin (U.S. Pat. No. 5,955,509) have described a type of pH-dependent micelles with a polyelectrolyte core. These micelles are composed of the diblock copolymers poly(vinyl N-heterocycle)-block-poly(alkylene oxide). Such copolymers are positively charged at acidic pH due to the protonation of the nitrogen atoms, and thus exist as unimers in acidic solutions. At high pH, the unprotonated copolymers self-associate into polymeric micelles. These micelles are primarily intended to deliver their contents at low pH, since the dissociation of the supramolecular assembly under acidic conditions allows a drug to be released. Such conditions may be found, for example in tumors. If intended to be administered by the oral route, these micelles would rapidly release their contents in the stomach because of its acidic pH. Therefore, for oral delivery, they should be formulated using an enteric coating to prevent premature drug leakage.

A potential problem with ionizable copolymers is the possibility of forming, at acidic pH, intra and intermolecular hydrogen bonding between the protonated and the non-ionizable hydrophilic blocks which might lead to the formation of an insoluble complex. This has been recently described by Lele et al. *J. Controlled Release* (2000) 69, 237–248, between poly(acrylic acid) and poly(ethylene glycol). Precipitation of the micelles at acidic pH could potentially compromise the efficacy of the system when oral delivery is envisaged.

PICM have a block or graft copolymer architecture and consist of a polyelectrolyte linked to a non-ionic water-soluble polymer. They bind with charged compounds due to electrostatic interactions with the polyelectrolyte (see, e.g., Kataoka et al. *Macromolecules* (1996) 29, 8556–8557). The complexes self-assemble into micelle-like structures which have a hydrophobic core from neutralized polyelectrolyte and counterion, and hydrophilic corona. PICM show improved solubility compared with other electrostatic complexes. Furthermore, they show reduced affinity for plasma components and can protect active compounds such as DNA against enzymatic degradation.

Although, PICM hold great promise as carriers for a variety of selected from the group consisting of ionizable and permanently-charged diblock copolymers, ionizable and permanently-charged multiblock copolymers, and ionizable and permanently-charged random copolymers with grafted hydrophilic and essentially non-ionic oligomers or polymers compounds, such as charged drugs and nucleic acids, some important issues still remain to be addressed. For instance, the stability of the polymeric micelles is influenced by various factors such as concentration, temperature and chemical structure of the polymer. In particular, the presence of salts is a key parameter for the dissociation of PICM since Coulombic interactions between charged segments are screened by the added salt. To overcome this problem, polymeric micelles can be stabilized by cross-linking the core or shell (see, e.g., Kakizawa et al. *J. Am. Chem. Soc.* (1999) 121, 11247–11248). However, cross-linking the core or shell can potentially chemically alter the active agent and/or excessively slow down its release from the micelles.

DESCRIPTION OF THE PRIOR ART

U.S. Pat. No. 5,693,751 teaches the preparation of polymeric micelles composed of a water-soluble block copolymer having a hydrophilic segment and a hydrophobic pharmacological-functioning segment to a side chain of which a drug is covalently bonded.

U.S. Pat. No. 5,702,717 teaches the preparation of a solution comprising a drug and a block amphiphilic copolymer of poly(ethylene glycol) and poly(α-hydroxy acids)or poly(ethylene carbonates). These copolymers are not polyelectrolytes.

U.S. Pat. No. 5,939,453 teaches the preparation of polymeric micelles and bioerodible drug delivery matrix using poly(ethylene glycol)-poly(orthoester) diblock and triblock copolymers. The principal novelty of this invention relies on the use of poly(orthoester) as the hydrophobic, bioerodible segment. These block copolymers are neither ionizable or permanently charged.

U.S. Pat. No. 5,786,387 teaches the preparation of supramolecular assemblies using lipid double chain derivatives containing poly(oxyethylene) for drug delivery applications. These block copolymers are neither ionizable or permanently charged. They efficiently are able to avoid the reticuloendothelial system and possess a long circulation time.

U.S. Pat. No. 5,840,319 teaches the preparation of polymeric micelles using polyether block copolymers having a critical micelle concentration of no more than 0.5% (w/w) at 37° C. in an isotonic aqueous solution. The formulation also contains a chemotherapeutic agent.

U.S. Pat. No. 5,770,627 teaches the preparation of hydrophobically-modified bioadhesive polyelectrolytes. These polyelectrolytes can form micellar structures in aqueous solutions (example 6) and be loaded with an active agent. The polyelectrolyte can be a graft or block copolymer. The outer shell is ionizable since it contains carboxylic acid groups whereas the inner core consists of a homopolymer, copolymer, unsaturated or saturated alkyl chains, or other hydrophobic moities. Methods of administering such agents to an animal are disclosed.

U.S. Pat. No. 5,955,509 relates to the use of poly(vinyl N-heterocycle)-block-poly(alkylene oxide) copolymers in micelle containing pharmaceutical formulations. The copolymers advantageously respond to pH differences in the environment to which they are exposed forming micelles at higher pH values. The micelles, which comprise a therapeutic compound and a copolymer, deliver drug in a pH dependent manner.

U.S. Pat. No. 5,929,177 provides a block polymer which has functional groups on both ends thereof, and which comprises hydrophilic/hydrophobic segments. As for the functional groups on its both ends, the block polymer has amino group, carboxyl group or mercapto group on the alpha terminal, and hydroxyl group, carboxyl group, aldehyde group or vinyl group on the omega terminal. Hydrophilic segment comprises polyethylene oxide, while hydrophobic segment is derived from lactide, lactone or (meth)acrylic acid ester. The block polymer of this invention forms a polymeric micelle which is usable as bio-compatible materials.

U.S. Pat. No. 5,925,720 provides a heterotelechelic oligomer or polymer which can be prepared by means of living polymerization and which can form stable micelles in an aqueous solvent. In this invention, there is no reference to stabilization of a polyelectrolyte micelle core.

U.S. Pat. No. 5,656,611 relates to compositions for stabilizing polynucleic acids using polyionic complexes. In one aspect the invention provides a polynucleotide complex between a polynucleotide and a block copolymer comprising a polyether block and a polycation block.

U.S. Pat. No. 6,217,912 provides a biodegradable composition suitable for delivering a gene into a cell.

U.S. Pat. No. 6,221,959 provides composition for stabilizing polynucleic acids and increasing the ability of polynucleic acid to cross cell membranes and act in the interior of a cell. In one aspect the invention provides a polynucleotide complex between a polynucleotide and certain polyether block copolymer.

U.S. Pat. No. 5,510,103 relates to drug carriers composed of a block copolymer having hydrophilic and hydrophobic segments, a polymeric type drug comprising hydrophobic drugs trapped by physical treatments in said drug carrier and methods for trapping hydrophobic drugs in the carrier.

What is lacking in the art are water-soluble supramolecular assemblies having a physically-stabilized polyelectrolyte core and an uncharged hydrophilic shell and techniques for their preparation.

SUMMARY OF THE INVENTION

The present invention is directed toward water-soluble supramolecular self-assemblies and a process for their preparation via micellization of polyelectrolytes through the use of hydrophobic monomeric units. In this invention the polyelectrolyte segment ultimately forms the core of the supramolecular assembly whereas the shell consists of uncharged hydrophilic polymers or oligomers. It has been determined that the inclusion of the hydrophobic co-monomers to the polyelectrolyte segment forming the micelle core leads to a structure of enhanced stability. Such co-monomers, by increasing the attractive forces between the segments of the core, stabilize the micelles and/or decrease the interaction between the ionizable or permanently-charged segment and non-ionizable segment of the copolymer.

Accordingly, it is an objective of the instant invention to provide a stabilized supramolecular assembly and a process for its production.

It is a further objective of the instant invention to provide, also through the use of hydrophobic monomers, pH-dependent polymeric micelles or polyion complexes which exhibit reduced interaction between the ionizable or permanently-charged segment and the non ionizable segments of the copolymer outer shell.

It is yet another objective of the instant invention to provide a pH dependent micellar vehicle, suitable as a carrier for pharmacological constituents which is not subject to the untoward formation of insoluble complexes.

It is a still further objective of the invention to teach a process for preparing stabilized supramolecular assemblies having a polyelectrolyte core, through the use of hydrophobic monomeric units.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
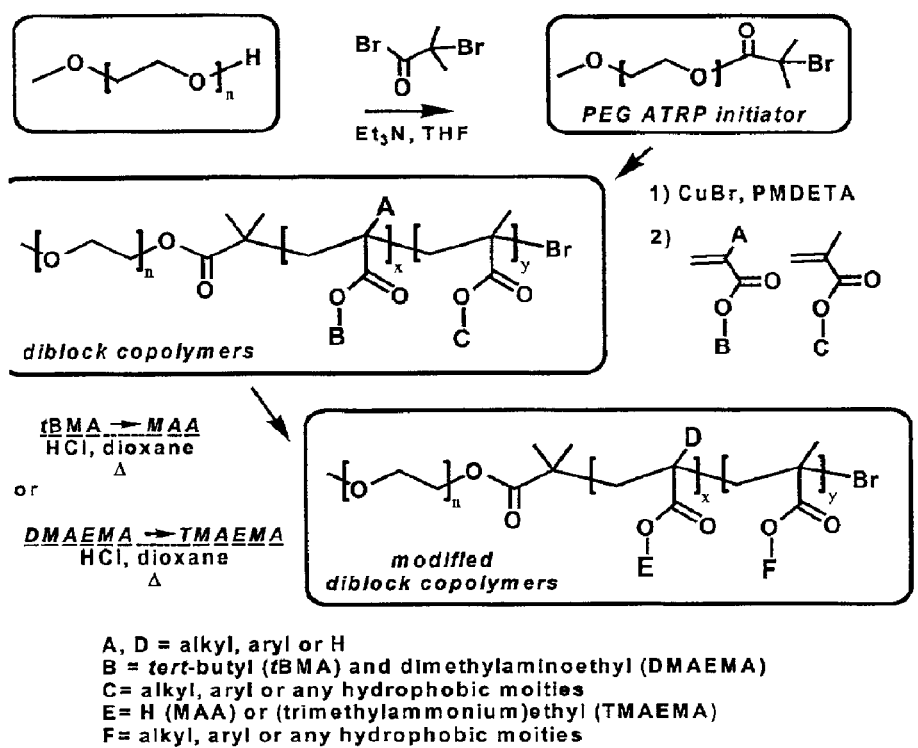
FIG. 1 is a synthetic route for the preparation of block copolymer, possessing a hydrophobized polyelectrolyte block.

In the present invention, the terms "water-soluble self-assemblies" and "micelles" are equally employed although the proposed structures may not necessarily correspond to the true definition of micelles.

Micelle formation occurs as a result of two forces. One is an attractive force that leads to the association of molecules, while the other is a repulsive force that prevents unlimited growth of the micelles to a distinct macroscopic phase. Amphiphilic copolymers self-associate when placed in a solvent that is selective for either the hydrophilic or hydrophobic polymer.

The micellization process of amphiphilic copolymers is similar to that for low molecular weight surfactants. At very low concentrations, the polymers exist only as single chains. As the concentration increases to reach a critical value called the critical association concentration ("CAC"), polymer chains start to associate to form micelles in such a way that the hydrophobic part of the copolymer will avoid contact with the aqueous media in which the polymer is diluted. Amphiphilic copolymers usually exhibit a CAC which is much lower than that of low molecular weight surfactants. For example, the CAC of PEO-PBLA and PNIPA-PSt are between 0.0005–0.002%. Some amphiphilic copolymers, however, exhibit much higher CAC, reaching up to 0.01–10% in the case of poloxamers. Amphiphilic copolymers with high CAC may not be suitable as drug targeting devices since they are unstable in an aqueous environment and are easily dissociated upon dilution.

Micelles can be targeted to specific cells or tissues via the inclusion of targeting ligands, e.g. monoclonal antibodies, lectins, sugars, vitamins, peptides or immunologically distinct fragments thereof or the like moieties which provide the micelles with an ability to preferentially concentrate in a particular target area.

The micellization of amphiphilic copolymers can result in two different types of micelles depending on whether the hydrophobic chain is randomly bound to the hydrophilic polymer or grafted to one end of the hydrophilic chain. Micelles formed from randomly modified polymers are generally smaller than end-modified polymers. The micellar size is mainly determined by the hydrophobic forces which sequester the hydrophobic chains in the core, and by the excluded volume repulsion between the chains which limits their size. The difference in the balance of these two forces in random and end-modified copolymers may account for their different size.

Determination of Critical Association Concentration (CAC):

Light scattering is widely used for the determination of the molecular weight and aggregation number of micelles. The onset of micellization can, however, be detected only if the CAC falls within the sensitivity of the scattering method. This is rarely the case for polymers in water. Gel permeation chromatography (GPC) under aqueous conditions can be employed since single chains and micellar fractions of copolymers exhibit different elution volumes. It is also possible to simultaneously determine by GPC the molecular weight of the micelles and their aggregation number.

A preferred method to determine the CAC involves the use of fluorescent probes, among which pyrene is widely used. Pyrene is a condensed aromatic hydrocarbon that is highly hydrophobic and sensitive to the polarity of the surrounding environment. Below the CAC, pyrene is solubilized in water, a medium of high polarity. When micelles are formed, pyrene partitions preferentially toward the hydrophobic domain afforded by the micellar core, and thus experiences a nonpolar environment. Consequently, numerous changes such as an increase in the fluorescence intensity, a change in the vibrational fine structure of the emission spectra, and a red shift of the (0,0) band in the excitation spectra are observed. The apparent CAC can be obtained from the plot of the fluorescence of pyrene, the $I_1/I_3$ ratio from emission spectra or the $I_{338}/I_{333}$ ratio from the excitation spectra versus concentration. A major change in the slope indicates the onset of micellization. Changes in anisotropy of fluorescent probes have also been associated with the onset of micellization. E.g. see Jones and Leroux *Eur. J. Pharm. Biopharm.* (1999) 48, 101–111.

Polymeric micelles such as those of the compositions of the invention are characterized by their small size. Besides being needed for extravasation of the carrier materials, this small size permits the sterilization of the composition to be effected simply by filtration, and minimizes the risks of embolism in capillaries after intravenous injection. Micellar size depends on several factors including copolymer molecular weight, relative proportion of hydrophilic and hydrophobic chains and aggregation number.

Micellar diameter and size polydispersity can be obtained directly in water or in an isotonic buffer by dynamic light scattering (DLS). Micelle size can also be estimated by methods such as atomic force microscopy (AFM), transmission electron microscopy (TEM) and scanning electron microscopy (SEM). These methods allow the characterization of the micelle shape and size dispersity. Ultracentrifugation velocity studies are sometimes performed to assess the polydispersity of polymeric micelles.

Loading of one or more pharmacological constituents, e.g. various therapeutic agents, drugs, peptides, proteins, genetic material (e.g. oligonucleotides), genetically altered constituents, polyionic constituents and the like, into the micelles can be realized according to techniques well known to one skilled in the art. For example, drugs can be incorporated into the polymeric micelle compositions of the invention by means of chemical conjugation or by physical entrapment through dialysis, emulsification techniques, simple equilibration of the drug and micelles in an aqueous medium or solubilization of a drug/polymer solid dispersion in water.

Therapeutic agents which may be used are any compounds, including the ones listed below, which can be entrapped, in a stable manner, in polymeric micelles and administered at a therapeutically effective dose. Preferably, the therapeutic agents used in accordance with the invention are hydrophobic or polyionic (e.g. DNA). Suitable drugs include antitumor compounds such as phthalocyanines (e.g. aluminum chloride phthalocyanine), anthracyclines (e.g. doxorubicin), poorly soluble antimetabolites (e.g. methotrexate, mitomycin, 5-fluorouracil) and alkylating agents (e.g. carmustine). Micelles may also contain taxanes such as paclitaxel.

Additional drugs which can be contained in micelles are conventional hydrophobic antibiotics and antifungal agents such as amphotericin B and itraconazole, poorly water-soluble immunomodulators such as cyclosporin, poorly water-soluble antiviral drugs such as HIV protease inhibitors and poorly water-soluble steroidal (e.g. dexamethasone), and non-steroidal (e.g. indomethacin) anti-inflammatory drugs.

Hydrophilic compounds such as proteins may also be incorporated in the polymeric micelle compositions of the invention. The incorporation of such hydrophilic species may, however, require the chemical hydrophobization of the molecule or a particular affinity for the hydrophilic shell. Polyionic compounds (e.g. antisense oligonucleotides, genome fragments, peptides) can be incorporated into micelles through the formation of PICM via electrostatic interaction with an oppositely charged block polyelectrolyte.

The polymeric micelle compositions of the invention are suitable for use in a variety of pharmaceutical fields, such as oral delivery, sustained release and site-specific drug targeting. Preferably, the micelles of the invention are used as a transport for water-insoluble and polyionic compounds. Included within the scope of the invention are supramolecular assembly compositions comprising a suitable targeting ligand.

Without intending to be limited to a particular synthesis procedure, block polyelectrolytes useful in the present invention are most preferably prepared by "living"/controlled radical polymerization (LCRP), such as atom transfer radical polymerization (ATRP) (see Coessens et al., *Prog. Polym. Sci.* (2001) 26, 337–377) or nitroxide-mediated radical polymerization (NMP) (see Benoit et al. *J. Am. Chem. Soc.* (1999), 121, 3904–3920). However, any alternative procedure such as other living radical polymerizations or condensation of preformed functionalized polymers could also be used. On the other hand, (i) ionizable and permanently-charged multiblock copolymers, (ii) ionizable and permanently-charged amphiphilic random copolymers with grafted hydrophilic oligomers (or polymers) could be used instead of block copolymers for diverse applications within the scope of the presently disclosed invention.

The radical initiator for the synthesis of the polymer by ATRP can be any appropriately functionalized molecule (e.g. poly(ethylene glycol) (PEG), PVP). The initiator bears an halogeno functionality that can be activated for ATRP (see Coessens et al., *Prog. Polym. Sci.* (2001) 26, 337–377). Without intending to be limited to any particular substituent, this functionality can be a 2-halogenoisobutyrylate derivative, 2-halogenopropionate derivative, 2-halogenoacetate derivative or 1-(halogenomethyl)benzene derivative. For other types of polymerizations (e.g. NMP), this functionality is appropriately chosen according to the used monomers.

The catalyst for the ATRP usually includes a metallic salt and a ligand. The ligand is used for the solubilization of the salt in organic solvent and/or to activate the redox reaction of the metal present in the salt. The salt activates the radical initiator for the ATRP. Without intending to be limited to any particular salt, the latter can be copper(I) bromide, copper(I) chloride or copper(I) thiocyanate, iron(II) and nickel(0 or I) compounds. The ligand can include 2,2'-bipyridine derivatives or bis(dimethylamino) compounds (e.g. N,N,N',N',N'',N''-pentamethyldiethylene-triamine (PMDETA).

Suitable polyelectrolyte compounds useful in the preparation of supramolecular self-assemblies may be selected from the group consisting of diblock copolymers including ionizable units, permanently charged units or mixtures of ionizable and permanently charged units, multiblock copolymers including ionizable units, permanently charged units or mixtures of ionizable and permanently charged units, and random copolymers with grafted hydrophilic and essentially non-ionic oligomers or polymers, said random copolymers including ionizable units, permanently charged units or mixtures of ionizable and permanently charged units.

The diblock copolymers generally consist of two blocks, one of which is hydrophilic and generally uncharged and the other containing at least one compound selected from the group consisting of ionizable and permanently-charged repeating units (or combinations thereof) in combination with essentially hydrophobic, e.g. hydrophobic or relatively hydrophobic non-ionic monomers. Ionizable units refers to repeating units that can be transformed from a non-ionic to a charged state via an external stimulus (e.g. pH or chemical reaction). Permanently charged units refers to repeating units that are in fact electrostatically charged irrespective of the external conditions.

The ionizable and/or permanently-charged block, bearing hydrophobic repeating units, can be synthesized from vinyl monomers, vinyl oligomers or eventually vinyl polymers. These hydrophobic monomers/oligomers/polymers can be acrylate, acrylamide, alkylacrylate, alkylacrylamide, arylacrylate and arylacrylamide derivatives for which the alkyl and aryl term stands for aliphatic or aromatic moieties respectively (e.g. methacrylate, methacrylamide derivatives.) The hydrophobic compound can also be a biodegradable polyester such as vinyl-terminated poly (lactide) and vinyl-terminated poly($\epsilon$-caprolactone). The ionizable monomers could be alkylacrylic acid derivatives, (aminoalkyl)acrylate or (aminoalkyl)alkylacrylate derivatives. The acidic or basic units of the polymer chain can be derived from a non-ionizable precursor (e.g. tert-butylmethacrylate), which is cleaved into an acidic moiety.

The hydrophilic block can be synthesized from vinyl monomers, vinyl oligomers or eventually vinyl polymers. These hydrophilic monomers/oligomers/polymers can be acrylate, acrylamide, alkylacrylate and alkylacrylamide (e.g. PEG methacrylate and N-(2-hydroxypropyl)acrylamide). On the other hand, the hydrophilic block can also originate from a block radical macroinitiator based on PEG or PVP derivatives.

Non biodegradable ionizable and/or permanently-charged copolymers that are intended to be administered parenterally, should have a molecular weights not exceeding 40,000. There is no restriction on molecular weights for biodegradable or non-biodegradable ionizable copolymers, which are used orally or locally.

The loading of poorly water-soluble and non-ionic drugs should be done in an organic solvent, or in aqueous solutions at a pH where the core is uncharged or mostly uncharged. Charged drugs should be loaded under conditions (e.g. pH) where electrostatic interactions with the ionizable or permanently-charged segment are possible.

EXAMPLES

Abbreviations:

The subscript text indicates the ratio in a polymeric segment. The letter b features that polymers and/or polymeric arms are based on a diblock copolymeric structure. The term co means the repeating units are disposed randomly along the polymeric segment.

Example 1

Synthesis of Poly(ethylene glycol)-block-poly(N, N-dimethylaminoethanemethacrylate-co-ethylmethacrylate) with a Ratio for DMAEMA/EMA of 30/70.

PEG-b-P (DMAEMA$_{30}$-co-EMA$_{70}$)
Materials:

All products were purchased from Aldrich (Milwaukee, Wis.). Copper(I) bromide (99.99% Grade), 2-bromoisobutyryl bromide, anhydrous triethylamine and N,N,N',N',N'',N''-pentamethyldiethylenetriamine (PMDETA) were used without further purification. Poly(ethylene glycol) monomethyl ether (MeO-PEG-OH, $M_n$: 2000) was dried with toluene by an azeotropic distillation before use. Ethyl methacrylate (EMA) and 2-(N,N-dimethylamino)ethyl methacrylate (DMAEMA) were used as vinyl monomers and distilled before polymerization. Prior to use, tetrahydrofuran (THF) was distilled over sodium, using benzophenone as drying indicator.

Synthesis of PEG ATRP Macroinitiator (α-(2-bromoisobutyrylate)-ω-methylPEG):

As exemplified in FIG. 1, to a solution of MeO-PEG-OH ($M_n$: 2000, 10 g, 0.005 mol) and triethylamine (1.0 g, 0.01 mol) in 70 mL of anhydrous THF, slightly cooled in a water-ice bath, was slowly added 2-bromoisobutyryl bromide (4.3 mL, 0.035 mol). The solution was then warmed to room temperature and stirred for 24 h. The mixture was poured into water and extracted with methylene chloride. The organic extracts were washed successively with a HCl 1M and NaOH 1M solution (containing NaCl), and dried over magnesium sulfate. The solvent was removed under reduced pressure. The crude was dissolved in a minimum of methylene chloride, and then precipitated in diethyl ether. The title compound was recovered by simple filtration. Yield: 70% after precipitation. White solid. M.P. 60–65° C.

$^1$H NMR (δ, ppm, CDCl$_3$): 4.18 (2H); 3.50 (188H); 3.23 (3H, s); 1.80 (6H, s).
ATRP:

The ATRP of monomers was carried out in bulk and in solution, using a-(2-bromoisobutyrylate)-w-methyl-PEG as ATRP macroinitiator. The PEG ATRP macroinitiator (1 eq.) was added to a solution containing PMDETA (1.1 eq.), Cu(I)Br (1.1 eq.), EMA (14eq) and DMAEMA (6 eq) in THF (0.8 M). The mixture was degassed with argon for 15–20 mm at room temperature and was then heated to 60° C. overnight. After the polymerization, the mixture was poured in THF, containing 10% of methanol. The resulting polymers were filtered on silica gel, with THF as eluent, to remove copper bromide. Finally, polymers were dialyzed (SPECTRA/POR NO.1, molecular weight cutoff 6000–8000) against water during 48 h and then freeze-dried.

Yield: 98%.

Poly(ethylene glycol)-block-poly(N, N-dimethylaminoethanemethacrylate-co-ethylmethacry-late). PEG-b-P (DMAEMA$_{30}$-co-EMA$_{70}$)

$^1$H NMR (d, ppm, CDCl$_3$): 4.30(18H); 4.04 (32H); 3.60 (182H); 3.38 (3H); 2.69 (54H), 2.05–1.87 (42H); 1.43 (6H); 1.26 (56H); 1.05 and 0.88 (73H).

Polymer and Micelle Characterization:

$^1$H and $^{13}$C NMR spectra were recorded on a Bruker AMX300 and ARX400 in deuterated chloroform (CDCl$_3$) and methanol (CD$_3$OD) (CDN Isotopes, Canada) at 25° C. Number- ($M_n$) and weight-average ($M_w$) molecular weights were determined by size exclusion chromatography (SEC) with an Alliance GPCV2000 (Waters, Milford, Mass.) and by nuclear magnetic resonance spectroscopy ($^1$H-NMR). Particle sizes were evaluated by dynamic light-scattering. The apparent CAC was measured by a steady-state pyrene fluorescence method.

Results:

Copper (I) bromide-pentamethyldiethylenetriamine (CuBr-PMDETA) was used as catalyst and gave yields of polymerization approaching 100% in THF. The reactivities of EMA and DMAEMA in THF were similar, with a $k^{app}$ of $1.95 \times 10^{-4}$ Lmol$^{-1}$s$^{-1}$. All monomers were completely consumed after 5 h and the $M_n$ obtained experimentally were close to the theoretical values (Table 1). Moreover, the polydispersity index (PI) was approximately 1.4 and corresponded approximately to the polydispersity of PEG macroinitiator used for the preparation of PEG-b-P (DMAEMA$_{30}$-co-EMA$_{70}$)

TABLE 1

$M_n$ and $M_w$ of P (DMAEMA$_{30}$-co-EMA$_{70}$).

| Copolymers | $M_n$ Theo | $M_n$ NMR | $M_n$ SEC | PI |
|---|---|---|---|---|
| PEG-b-P(DMAEMA$_{30}$-co-EMA$_{70}$) | 4690 | 4900 | 4700 | 1.4 |

Figure 2:
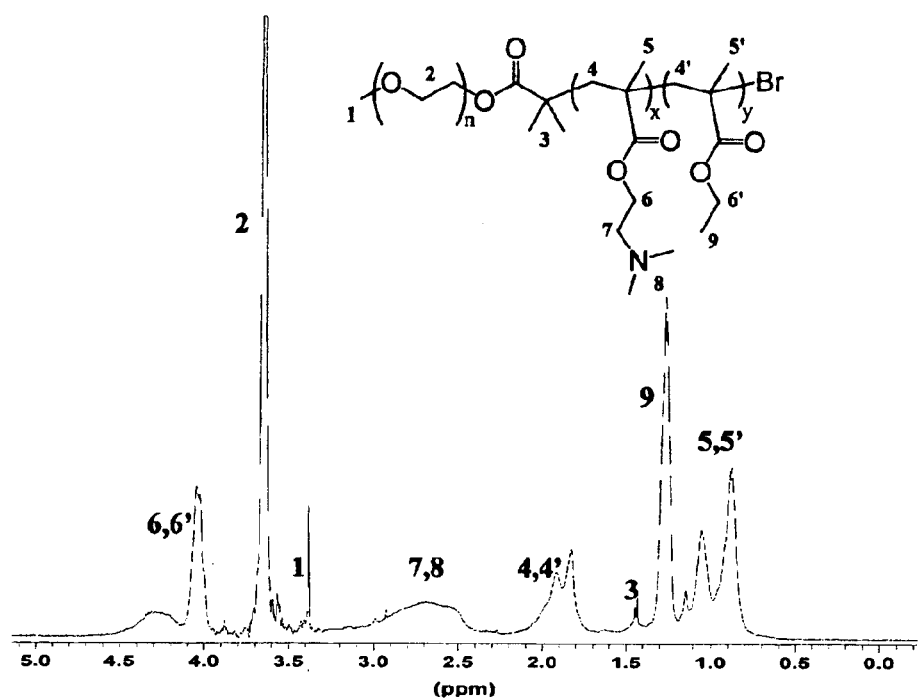
FIG. 2 is the $^1$H NMR spectrum of PEG-b-P(DMAEMA$_{30}$-co-EMA$_{70}$) in CDCl$_3$.

FIG. 2 shows the $^1$H NMR spectrum of PEG-b-P (DMAEMA$_{30}$-co-EMA$_{70}$). The terminal methoxy group of PEG (signal 1, 3.35 ppm), was used as a reference to calibrate the integration of the other signals. The integration of signal 2 showed that the degree of polymerization (DP) of ethylene oxide (PEG chains) was approximately 45 in each copolymer and corresponded to the DP of the commercial PEG used. The narrow signal of the PEG ATRP macroinitiator at 1.80 ppm, assigned to the methyl of the bromoisobutyryl group, decreased rapidly at the beginning of the polymerization and shifted within 10 min to about 1.4 ppm (signal 3), confirming that all PEG chains were coupled to the polyvinyl segments. The signals assigned to the methylene groups in the backbone were observed at 1.8 ppm (signals 4 and 4') and are represented by 3 successive peaks of decreasing intensity. The polymethacrylate derivatives presented two signals assigned to the methyl attached to the backbone (signals 5 and 5'). The ratios were determined using the signals 7, 8 and 9.

The CAC of PEG-b-P(DMAEMA$_{30}$-co-EMA$_{70}$) was determined in water and phosphate buffered saline (PBS, pH 7.4) to verify whether salts could interfere with self-assembling. A remarkable fact was that the PEG-b-P(DMAEMA$_{30}$-co-EMA$_{70}$) showed a low CAC in water and PBS, despite the presence of DMAEMA which is ionized in these aqueous solutions (Table 2). This could be explained by the presence of EMA in the polymer. Interestingly, the CAC was not significantly affected by the presence of salts in water. This is an important issue, since a common drawback about PICM is their relative poor stability in physiological media. Accordingly, the stability of PICM can be easily increased by introducing a hydrophobic comonomer in the polymer backbone. With regard to the micelle sizes for PEG-b-P(DMAEMA$_{30}$-co-EMA$_{70}$) the nature of the aqueous solution (water vs PBS) seemed to influence the proportion of secondary aggregates (Table 2).

TABLE 2

Micellar properties of PEG-b-P (DMAEMA$_{30}$-co-EMA$_{70}$)

| Copolymer | DP of the polyvinyl block | CAC (mg/L) ± 10% | Micelle size (nm) SD ± 25% | Size Peak amount |
|---|---|---|---|---|
| PEG-b-P (DMAEMA$_{30}$-co-EMA$_{70}$) In water | 20 | 2 | 392<br>22 | 79%<br>21% |
| PEG-b-P (DMAEMA$_{30}$-co-EMA$_{70}$) In PBS | 20 | 3 | 280<br>79 | 24%<br>76% |

Example 2
Synthesis of a Diblock Copolymer Containing Methacrylic Acid Units as Ionizable Units:
PEG-b-P(EA$_{50}$-co-tBMA$_{50}$) (precursor)
PEG-b-P (EA$_{50}$-co-MAA$_{50}$)
Materials, Synthesis of PEG-ATRP Macroinitiator and ATRP:

Carried out as described in Example 1. However, the only difference was 5 eq. of EMA and 5 eq. of tert-butyl methacrylate (tBMA) versus 1 eq. of PEG-ATRP macroinitiator were used for the polymerization of PEG-b-P(EA$_{50}$-co-tBMA$_{50}$). In the case of PEG-b-P(MAA), only the TBMA monomer (18 eq.) was used. (FIG. 1)
Transformation of tBMA into MAA:

The ester groups, bearing a tert-butyl chain (tBMA), were transformed into carboxylic acid groups, by the cleavage of tert-butyl in acidic conditions. To a solution of the polymers having tBMA units (7.7 mmol) in dioxane (2.6 M) was added concentrated HCl (32 mmol) for 5 h. The methacrylic acid derivatives were precipitated in diethyl ether and filtered. The polymers were dissolved in ethanol, dialyzed against water and freeze-dried.
Polymer and Micelle Characterization:

$^1$H and $^{13}$C NMR spectra were recorded on a Bruker AMX300 and ARX400 in CDCl$_3$, in CD$_3$OD and in D$_2$O (CDN Isotopes) at different pH, using very small amounts of HCl and NaOH. Mn and M$_w$ were determined by SEC with an Alliance GPVC2000 (Waters, Milford, Mass.) and by NMR spectroscopy. Hydrodynamic mean diameter and size distribution were determined at a 90° angle by DLS using differential size distribution processor intensity analysis (N4Plus, Coulter Electronics, Miami, Fla.). The apparent CAC was measured by a steady-state pyrene fluorescence method. The pH of self-association was determined by static light scattering at 480 nm, using a Series 2 Aminco fluorimeter. The pH of association was also determined by the steady-state pyrene fluorescence method. Poly(ethylene glycol)-block-poly(tert-butyl methacrylate) PEG-b-P (tBMA); M$_n$: 4560; Using tBMA as monomer:

$^1$H NMR (δ, ppm, CDCl$_3$): 4.10 (36H); 3.64 (181H); 3.37 (3H,s) 2.02–1.80 (36H); 1.44 (6H, s); 1.40 (162H, s); 1.13 (18H, s); 1.02 (36H, s)
Poly(ethylene glycol)-block-poly(methacrylic acid) PEG-b-P(MAA); M$_n$: 3180; Obtained from PEG-b-P(tBMA) After the Cleavage of tert-butyl Groups:

$^1$H NMR (δ, ppm, MeOD): 4.19 (36H); 3.66 (186H); 3,38 (3H); 2.02 (24H); 1.57 (2H); 1.16 (43H).
Poly(ethylene glycol)-block-poly(ethyl acrylate-co-tert-butyl methacrylate); PEG-b-P(EA$_{50}$-co-tBMA$_{50}$); M$_n$: 3600; Using tBMA and EMA as Monomers:

$^1$H NMR (δ, ppm, CDCl$_3$): 4.10 (12H); 3.66 (181H); 3.39 (3H); 2.10–1.70 (22H); 1.44 (54H); 1.28 (18H); 1.00 (22H).
Poly(ethylene glycol)-block-poly(ethyl acrylate-co-methacrylic acid); PEG-b-P(EA$_{50}$-co-MAA$_{50}$); M$_n$: 3400; Obtained from PEG-b-P(EMA$_{50}$-co-tBMA$_{50}$) After the Cleavage of tert-butyl Groups:

$^1$H NMR (δ, ppm, MeOD): 4.10 (12H); 3.63 (181H); 3.36 (3H); 2.20–1.70 (22H); 1.65 (6H); 1.26 (18H); 1.14 (22H).
Results:

Well-defined acidic (ionizable) copolymers, containing or not hydrophobic units were prepared by ATRP using a PEGylated ATRP macroinitiator. This macroinitiator was synthesized by coupling PEG monomethyl ether to 2-bromoisobutyryl bromide with a high yield. Copper (I) bromide-pentamethyldiethylenetriamine (CuBr-PMDETA) was used as catalyst and gave yields of polymerization approaching 100% in THF. The M$_n$ estimated by NMR were calculated from the terminal methoxy group of the PEG chain (~3.4 ppm). All monomers were completely consumed after 5 h and the M$_n$ obtained experimentally were close to the theoretical values. For all copolymers, the polydispersity was within the range of about 1.3 to about 1.5 (Table 3).

TABLE 3

Molecular weights of precursors of P (MAA) diblock copolymer derivatives

| Copolymer | M$_n$ Theo | M$_n$ NMR | M$_n$ SEC relative | M$_n$ SEC universal | M$_w$/M$_n$ |
|---|---|---|---|---|---|
| PEG ATRP macroinitiator | 2150 | 2250 | 2100 | 2200 | 1.3 |
| PEG-b-P (tBMA) | 4460 | 4560 | 3600 | 3900 | 1.5 |
| PEG-b-P (EA$_{50}$-co-tBMA$_{50}$) | 3360 | 3600 | 3700 | 4000 | 1.4 |

Figure 3:
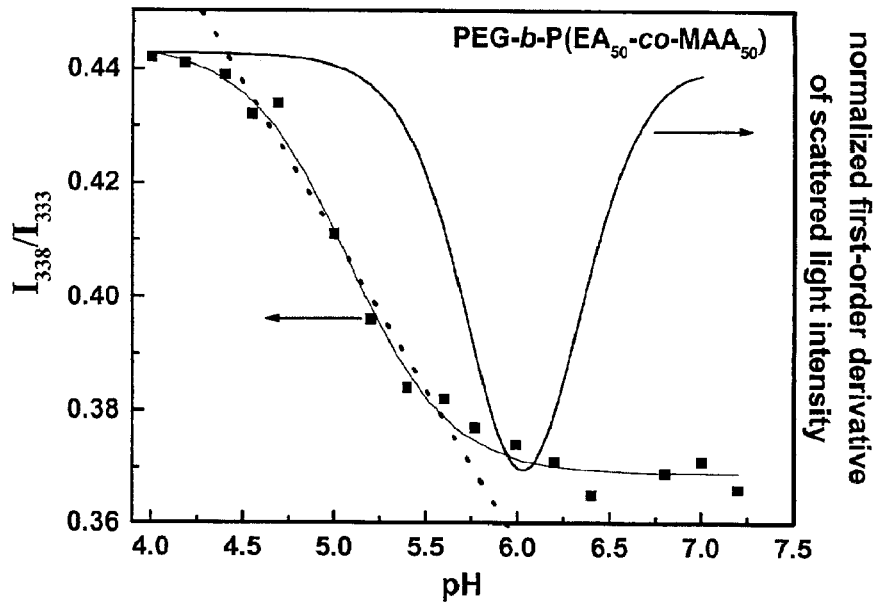
FIG. 3 shows the variation in light scattering and pyrene fluorescence $I_{338}/I_{333}$ ratio of a PEG-b-P(EA$_{50}$-co-MAA$_{50}$) aqueous solution as a function of pH.

The PEG-b-P(EA$_{50}$-co-tBMA$_{50}$) and PEG-b-P(tBMA) precursors were transformed into their respective P(MAA) derivatives by cleaving the tert-butyl groups in presence of hydrochloric acid in dioxane. The monomer ratios of the prepared copolyvinyl polymers corresponded approximately to the proportions of monomers used for the polymerization. The hydrophobic unit EA was incorporated in the polyvinyl segment, to increase hydrophobicity. At high pH values, the copolymers are fully ionized and should be in solution mostly as individual polymeric chains. As the pH is decreased, the protonation of the carboxylic groups should increase the hydrophobic character of the copolymer and induce chain aggregation. The pH of interchain association was determined at body temperature (37° C.) by static light scattering and by spectrofluorimetry, using pyrene as a probe (Table 2). FIG. 3 shows the ratio of fluorescence intensities (I$_{338}$/I$_{333}$) versus pH, and the first-order derivative of scattered light as a function of pH for PEG-b-P(EA$_{50}$-co-MAA$_{50}$). The polymeric chains associated at a pH value close to 6, as determined by both techniques (FIG. 3).

Interestingly, PEG-b-P(EA$_{50}$-co-MAA$_{50}$) remained soluble at acidic pH, indicating that the protonation of MAA units did not make the diblock copolymers precipitate. In the case of PEG-b-P(MAA), a diffuse precipitate appeared when the pH was decreased to around pH 3.5–4. It is known that acrylic acid polymeric derivatives interact through hydrogen bonding with PEG in acidic solutions, resulting in precipitation of the polymers. Without intending to be bound to any specific mechanism, we believe that in the presence of the hydrophobic ethyl acrylate comonomer the attractive forces between the protonated MAA and ethylene oxide units are sterically hindered. Accordingly, since PEG-b-P(EA$_{50}$-co-MAA$_{50}$) remains soluble at acidic pHs, it is possible that the MAA units become sequestered in the inner core of a supramolecular assembly (possibly micelles) which is stabilized by the PEG chains.

Figure 4:
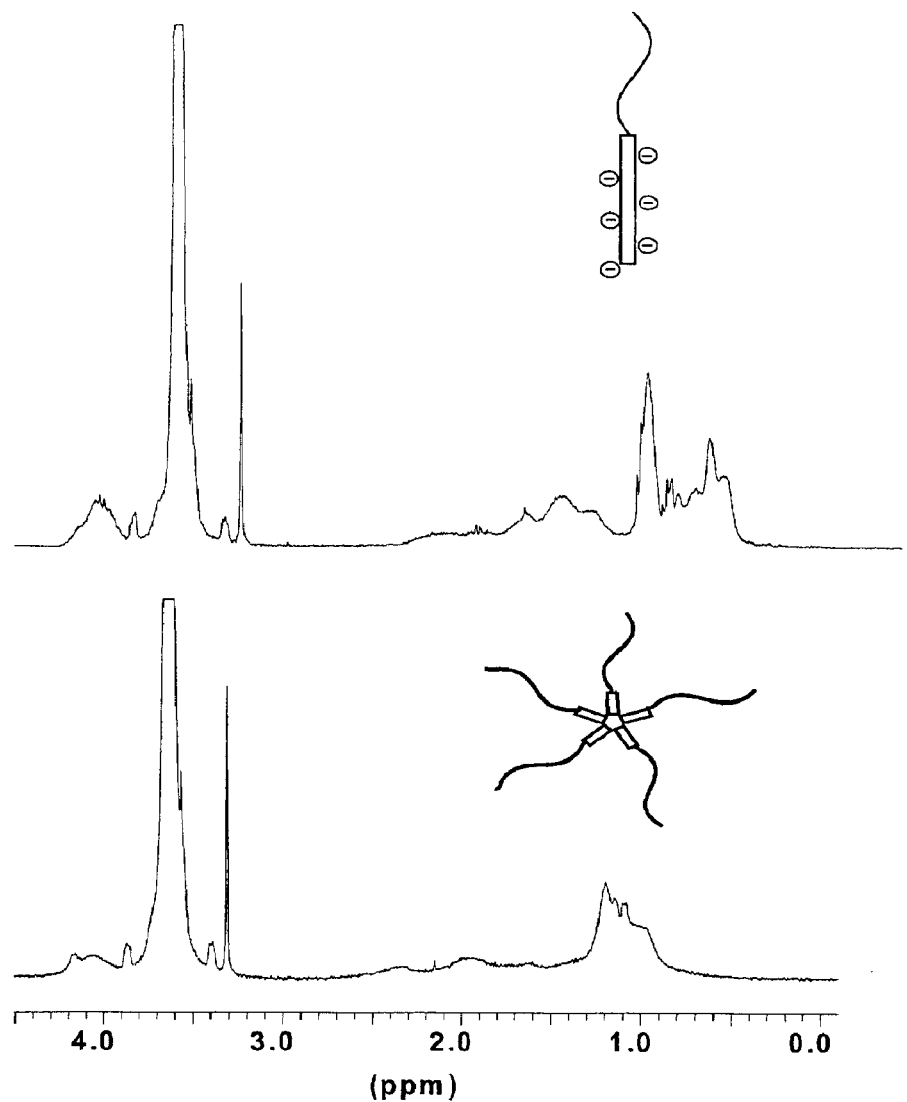
FIG. 4 shows the $^1$H NMR spectrum of PEG-b-P(EA$_{50}$-co-MAA$_{50}$) in D$_2$O at pH 10 (A) and at pH 3 (B).

To confirm the pH-dependent associative behavior of PEG-b-P(EA-co-MAA), its $^1$H NMR spectra were recorded in D$_2$O at pH 10 and 3 (FIG. 4). At pH 10 (FIG. 4A), the copolymer demonstrated all peaks proper to the PEG and the ionized parts, presenting integrations in accordance with the molecular weight ($M_n$). This suggests that all polymer chains were isolated from each other in water at high pH. However, at low pH (~3), the decreased peaks assigned to P(EA-co-MAA) segments indicated the presence of chain aggregation (FIG. 4B). Chain aggregation (into polymeric micelles) leads to the formation of a highly viscous internal core and, thus, to a partial suppression of the signals of EA and MAA units. Supporting these results, analysis by DLS revealed, at pH 3, the presence of a colloid population (215±50 nm), that was absent at pH 10.

TABLE 4

Determination of the aggregation pH of polymethacrylic acid derivatives

| Copolymer | Aggregation pH determined by fluorimetry | Aggregation pH determined by light scattering | Number of MAA per chains* |
|---|---|---|---|
| PEG-b-P (MAA) | 5.6 | 4.9 | 18 |
| PEG-b-P (EA$_{50}$-co-MAA$_{50}$) | 5.8 | 6.0 | 5 |

*Number of MAA units in the polyvinyl segment, evaluated by $^1$H NMR spectroscopy from the corresponding copolymers having tert-butyl groups.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The compounds, compositions, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. Multimolecular micelles consisting essentially of polyelectrolyte copolymers including at least one hydrophobic block and at least one hydrophilic block wherein:
   1) said at least one hydrophobic block comprises ionizable and/or charged repeating monomers in combination with nonionic hydrophobic repeating monomers; wherein the ionizable and/or charged repeating monomers include at least one compound selected from the group consisting of alkylacrylic acid derivatives, acrylic acid derivatives, aminoalkylacrylate derivatives, and (amino alkyl) alkylacrylate derivatives, and wherein the non-ionic hydrophobic repeating monomers include one or more hydrophobic vinyl compounds; and
   2) said at least one hydrophilic block, comprises a non-ionic hydrophilic polymer or oligomer that is polyethylene glycol or that is synthesized from hydrophilic vinyl monomers; and
   wherein said hydrophobic block comprising ionizable and/or charged repeating monomers in combination with the nonionic hydrophobic repeating monomers forms a micellar core and said hydrophilic block forms the exterior of the micelle.

2. The multimolecular micelles of claim 1 wherein each said polyelectrolyte copolymer is a graft copolymer wherein:
   1) said hydrophobic block serves as a backbone to which said hydrophilic polymers or oligomers are grafted, wherein said hydrophobic block comprises ionizable and permanently-charged amphiphilic random copolymers including at least one compound selected from the group consisting of alkylacrylic acid derivatives, acrylic acid derivatives, aminoalkylacrylate derivatives, and (amino alkyl) alkylacrylate derivatives in combination with said nonionic hydrophobic repeating monomers; or
   2) said hydrophilic block serves as a backbone to which one or more hydrophobic blocks of claim 1 are grafted.

3. The multimolecular micelle of claim 1 wherein:
   said one or more hydrophobic vinyl compounds are selected from the group consisting of acrylates, acrylamides, alkylacrylates, alkylacrylamides, arylacrylates, and arylacrylamides.

4. The multimolecular micelle of claim 3 wherein:
   said one or more hydrophobic vinyl compounds comprise at least one aliphatic or aromatic moiety selected from the group consisting of methacrylates and methacrylamides.

5. The multimolecular micelle of claim 3 wherein:
   said hydrophobic repeating monomers form at least one vinyl-terminated biodegradable polyester.

6. The multimolecular micelle of claim 1 wherein:
   said at least one hydrophilic block comprises at least one repeating unit selected from the group consisting of acrylates, acrylamides, alkylacrylates, alkylacrylamides, and N-vinyl-2-pyrrolidones.

7. The multimolecular micelles of claim 6, wherein:
   said hydrophilic block originates from a macroinitiator comprising a poly(ethylene glycol) or a poly (N-vinyl-2-pyrrolidone).

8. The multimolecular micelle of claim 2 wherein:

said one or more hydrophobic vinyl compounds are selected from the group consisting of acrylates, acrylainides, alkylacrylates, alkylacrylamides, arylacrylates, and arylacrylamides.

9. The multimolecular micelle of claim 8 wherein:

said one or more hydrophobic vinyl compounds comprise at least one aliphatic or aromatic moiety selected from the group consisting of methacrylates and methacrylamides.

10. The multimolecular micelle of claim 8 wherein:

said hydrophobic repeating monomers form at least one vinyl terminated biodegradable polyester.

11. The multimolecular micelle of claim 2 wherein:

said hydrophilic vinyl monomers are selected from the group consisting of acrylates, acrylamides, alkylacrylates, alkylacrylamides, and N-vinyl-2-pyrrolidones.

* * * * *